United States Patent
Yoon et al.

(10) Patent No.: US 7,387,895 B2
(45) Date of Patent: Jun. 17, 2008

(54) MONOCLONAL ANTIBODY SPECIFIC FOR PPAR GAMMA, HYDRIDOMA CELL LINE PRODUCING THE SAME, AND METHOD FOR DETECTING REGULATOR RELATED TO DISEASES, INCLUDING INFLAMMATION, CANCER AND METABOLIC DISEASES, USING THE SAME

(75) Inventors: Doyoung Yoon, Daejeon (KR); Haesook Lee, Daegu (KR); Minchul Cho, Daejeon (KR); Kyungae Lee, Chungnam (KR); Kyungjoo Cho, Daejeon (KR); Jeongwoo Kang, Jeonju (KR); Junghyun Shim, Daejeon (KR); Jongseok Lim, Daejeon (KR); Jintae Hong, Cheongju (KR); Heegu Lee, Daejeon (KR); Yongkyung Choe, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 58 days.

(21) Appl. No.: 10/543,452

(22) PCT Filed: Oct. 16, 2003

(86) PCT No.: PCT/KR03/02157

§ 371 (c)(1), (2), (4) Date: Jul. 25, 2005

(87) PCT Pub. No.: WO2005/026336

PCT Pub. Date: Mar. 24, 2005

(65) Prior Publication Data

US 2006/0140938 A1 Jun. 29, 2006

(30) Foreign Application Priority Data

Sep. 16, 2003 (KR) .................... 10-2003-0064182

(51) Int. Cl.
*C12N 5/06* (2006.01)

(52) U.S. Cl. ............... 435/334; 530/387.7; 530/388.1; 530/388.22

(58) Field of Classification Search ............. 350/388.1; 435/334; 530/387.7, 388.22, 388.1
See application file for complete search history.

(56) References Cited

U.S. PATENT DOCUMENTS 6,365,361 B1   4/2002   Taniguchi et al.

OTHER PUBLICATIONS

Fundamental Immunology (William E. Paul, M.D. ed., 3d ed; 1993, p. 242).*
Cho et al., A Simple Elisa for Screening Ligands of Peroxisome Proliferator-Activated Receptor Gamma, Journal of Biochemistry and Molecular Biology, vol. 36(2):207-213, Mar. 2003.
Krey et al., Fatty Acids, Eicosanoids, and Hypolipidemic Agents Identified as ligands of Peroxisome Proliferator-Activated Receptors by Coactivator-Dependent Receptor Ligand Assay, Molecular Endocrinology, vol. 11(6) 779-791, Jun. 1997.
Kurosaki et al., Differential Effects of YM440 a Hypoglycemic Agent on Binding to a Peroxisome Proliferator-Activated Receptor Gamma and its Transactivation, Biochemical Pharmocology, vol. 65(5): 795-805.
Liu et al., A Homogeneous in Vitro Functional Assay for Estrogen Receptors: Coactivator Recruitment, Molecular Endocrinology, vol. 17(3): 346-355, Mar. 2003.

* cited by examiner

Primary Examiner—Stephen L. Rawlings
Assistant Examiner—Brad Duffy
(74) Attorney, Agent, or Firm—Sheridan Ross P.C.

(57) ABSTRACT

The present invention relates to a hybridoma cell line producing a PPAR gamma-specific monoclonal antibody, and a method for detecting a PPAR gamma ligand related to the progression of difficult diseases, such as cancer, inflammation and metabolic diseases obesity and diabetes), using the PPAR gamma-specific monoclonal antibody. This PPAR gamma-specific monoclonal antibody and the method for screening a PPAR gamma ligand using the monoclonal antibody will be commercially used for screening a PPAR gamma regulator related to diseases such as inflammatory, cancer and metabolic diseases, and also will serve as an useful tool for analyzing the function of such a ligand.

3 Claims, 6 Drawing Sheets

MONOCLONAL ANTIBODY SPECIFIC FOR PPAR GAMMA, HYBRIDOMA CELL LINE PRODUCING THE SAME, AND METHOD FOR DETECTING REGULATOR RELATED TO DISEASES, INCLUDING INFLAMMATION, CANCER AND METABOLIC DISEASES, USING THE SAME

TECHNICAL FIELD

The present invention relates to a PPAR gamma-specific monoclonal antibody, a hybridoma cell line producing the same, and a method for detecting a regulator related to diseases including inflammation, cancer and metabolic diseases, using the same.

BACKGROUND ART

The protein PPAR (peroxisome proliferator activated receptor) is known as a nuclear receptor. Peroxisome which is an intracellular organelle is involved in oxidation and present in the liver and kidneys at large amounts. Also it oxidizes an intracellular fatty acid to produce peroxides which serve to neutralize toxic substances. In addition, it has a function of decomposing excess hydrogen peroxide into water and oxygen by catalase, an oxidase. A peroxisome proliferator signifies a compound capable of increasing the number of peroxisomes, and includes fat and fatty acid, and fibrate and prostaglandin as hyperlipemia-treating agents.

Nuclear receptors having such peroxisome proliferators as ligands are collectively called PPARs, which are divided into PPAR alpha, PPAR delta/beta and PPAR gamma. As known in the art, PPAR alpha is mainly expressed in the liver, and involved in the oxidation of fatty acids or the neutralization of toxic substances, and related to inflammatory reaction. PPAR delta/beta is found to distribute uniformly and to be involved in embryonic development, and PPAR gamma is known to be involved in the differentiation and accumulation of fat cells.

It was recently found that the expression of PPAR gamma was increased in a differentiation process of a fat cell line into a fat cell, and that expression of PPAR gamma in fibroblast having no differentiation ability resulted in differentiation of the fibroblast into a fat cell. Particularly, PPAR gamma2 is divided into two isoforms and reported to be specifically expressed only in fat cells at large amounts. mRNA of mouse PPAR gamma1 is coded by eight exons, whereas mRNA of PPAR gamma2 is coded by seven exons. The 5' untranslated sequence of mRNA of mouse PPAR gamma1 is coded by two exons, whereas the 5' untranslated sequence of PPAR gamma2 and the additional N-terminal amino acids are coded by one exon. The two isoforms are yielded by alternative promoter use and different splicing, and increase the variety of ligands and make tissue-specific expression possible (Zhu Y et al., 1995).

Meanwhile, type 2 diabetes is characterized by the insulin resistance of skeletal muscle tissues, liver tissues and fat tissues, etc. In the early 1980's, among treating agents of type 2 diabetes, glitazones and the like belonging to thiazolidinediones (TZD) were first reported as a drug which allows glucose level to be reduced and insulin resistance to be improved without stimulating insulin secretion in an experimental rat model of type 2 diabetes.

As glitazones, treating agents of type 2 diabetes, are found to be PPRA gamma agonists (Lehmann J M et al, 1995), it is reported that PPRA gamma ligands (agonists) can improve insulin resistance.

This fact seems to prove the therapeutic effect of the PPAR gamma agonists and to suggest the utility of a system for screening diabetes-effective substances by ELISA, which was established by the present inventors.

Meanwhile, in order to examine how the activity of PPAR gamma in fat cells influences the metabolism of glucose in the muscles and liver, the mechanisms of PPAR gamma agonists as agents for improving diabetes will now be described. First, PPAR gamma protein in fat cells is known as regulating the release of endocrine signal molecules influencing the metabolism of glucose in the muscles and liver, such as cytokine TNF-α or leptin. Expression of the two signal molecules is inhibited by the PPAR gamma agonists in fat cells, and it was found that TNF-α resulted in the increase of insulin resistance and leptin interfered-with insulin signal transmission in any cells (Cohen B. et al., 1996; and Muller G. et al., 1997). This seems to increase insulin resistance. Thus, insulin resistance caused by such two signal molecules can be improved by the PPAR gamma agonists.

Second, there is the antihyperglycemic effect of PPAR gamma agonists. Generally, glucose and fatty acids compete with each other for an energy substrate in muscles, so that the increase of the amount of fatty acids results in the decrease of glucose consumption. Thus, it is believed that the increase of free fatty acids and the increase of glucose synthesis or gluconeogenesis are connected with each other. In this case, the PPAR gamma agonists stimulate fat cells to absorb and store fatty acids, thereby reducing the amount of circulating triglycerides and free fatty acids. Furthermore, the PPAR gamma agonists are known as having an indirect effect on glucose metabolism, reducing the level of fatty acids in the muscles or liver (Martin G. et al., 1998). Accordingly, the PPAR gamma agonists stimulate fatty acid flow from the muscles or liver to white fatty acids and show a dramatic effect on energy expenditure, thereby causing the reduction of gluconeogenesis in the liver and the increase of glucose consumption in muscles.

Finally, PPAR gamma is also expressed in the muscles and liver at a lower expression level than in fat cells and can show an effect of improving diabetes by its direct activation. Namely, it is reported that treatment of experimental rats deficient in fat tissues with troglitazone as a PPAR gamma agonist reduces hyperglycemia and increases insulin sensitivity. This mechanism can be regarded as the role of PPAR gamma agonists generated by a pathway separate from fat cells (Burant C F et al., 1997).

And the PPAR gamma agonists show a direct or indirect effect in various tissues including the muscles and liver.

Moreover, for atheromatous lesions, PPAR gamma is known as being expressed in macrophages including foam cells at a high level.

The foam cells generally means cholesterol-laden cells converted from macrophages embedded in the inner arterial wall. This conversion of the macrophages into the foam cells is regarded as a definite symptom of occurrence of arteriosclerosis.

The conversion process of the cells is known as having a connection with the internalization of oxLDL particles by scavenger receptors, such as CD36 (cell adhesion molecule) and scavenger receptor-A. It was recently reported that PPAR gamma was also closely connected with this process (Tontonoz P. et al., 1998).

For example, it is known that treatment of a human acute monocytic leukemia cell line (THP-1) with PPAR gamma and RXR alpha (retinoid X receptor alpha) agonists induces the expression of PPAR gamma2 and CD36 and promotes the absorption of oxLDL, and treatment of the aorta of experimental rats with the PPAR gamma agonist increases the expression of CD36. Particularly, 9-HODE and 13-HODE, two components of oxLDL, were found to be PPAR gamma agonists. Accordingly, PPAR gamma is an important component of oxLDL-PPAR gamma-CD36 contributing to the accumulation of lipids induced from oxLDL by macrophages. These results indicate that PPAR gamma agonists have the possibility of promoting the formation of foam cells, but clinical data show that glitazone protects patients with type 2 diabetes from arteriosclerosis which can frequently secondarily occur in these patients. This is because treatment of low density lipoprotein (LDL) receptor-deficient rats (arteriosclerosis model) with rosiglitazone and GW784 is known as inhibiting the formation of atheromatous lesion in spite of the increase of CD36 expression.

According to recent studies, it was found that the release of cholesterol from macrophages was controlled by ABCA1 (ATP binding cassette A1), a member of ATP binging cassettes (ABC) of energy-dependent transporter proteins, in which ABCA1 is mutated in patients with tangier disease caused by cholesterol accumulation in macrophages and other reticuloendothelial cells. The transcription of an ABCA1 gene is regulated by a nuclear oxysterol receptor LXR (liver X receptor), and PPAR gamma and LXR agonists act together to induce the expression of ABCA1 and to promote the release of cholesterol from macrophages and THP-1 cell lines induced from rat embryonic stem cells (Chawla A. et al., 2001).

Furthermore, the ABCA1 gene is known as a direct target gene of a PPAR gamma/RXR heterodimer and causes the expression of LXR-alpha when the activity of PPAR gamma is increased. This leads to the increase of ABCA1 expression and the release of cholesterol. In addition, PPAR gamma is known to regulate the introduction and release of cholesterol esters in macrophages. By this effect, oxLDL will be removed which increases the release of free cholesterol introduced to the liver, and causes aortic lesions by absorption into macrophages. Particularly, the PPAR gamma agonists seem to interfere with the development arteriosclerosis in vivo by producing HDL (high density lipoprotein) in the human and increasing the release of cholesterol from macrophages and endothelial cells.

Moreover, there is the broad role of PPAR gamma in the regulation of inflammatory reaction of monocytes/macrophages.

Treatment of PPAR gamma including 15d-PGJ2 and glitazone, with monocytes or macrophages, reduces the expression of pro-inflammatory cytokine such as TNF-alpha and IL-6 and inhibits the activity of macrophages. However, the PPAR gamma agonists induce an effect of inhibiting inflammatory reaction at a different concentration from a concentration required to activate PPAR gamma in cell-based assays. In addition, any potential PPAR gamma agonists have no effects, but 15d-PGJ2 is the most powerful inhibitor against the cytokine production of monocytes or macrophages in vitro. This suggests that the anti-inflammatory effect of the PPAR gamma agonists can be mediated by PPAR-independent mechanism. This hypothesis is supported by several recent studies. Namely, it was found that glitazone inhibited cytokine production in rats treated with LPS (lipopolysaccharide) and that several different PPAR gamma agonists (15D-PGJ2 and rosiglitazone) inhibited cytokine production even in embryonic stem cells having PPAR gamma+/+ or PPAR gamma± or PPAR gamma−/−, as in macrophages.

Meanwhile, 15d-PGJ2 was recently found to inhibit NF-κB activity (Rossi A. et al., 2000; and Straus D. S. et al., 2000). NF-κB causes acute inflammatory reaction by the covalent modification of its DNA-binding domain and IκB kinase as its regulatory subunit. This suggests that PPAR gamma is not substantially effective against acute inflammations caused by leucocytes.

Furthermore, hypertension is one of metabolic defects which often accompany obesity and type 2 diabetes, etc. Its pathogenesis is complex and connected with blood pressure dysregulation, insulin sensitivity, vascular function, and lipid metabolism.

Recent genetic analysis shows that a PPAR gamma dominant negative mutant is connected with severe hypertension Treatment of an animal model of hypertension with PPAR gamma agonists shows low blood pressure, but it is not yet known that the PPAR gamma agonists are involved in a mechanism forming the basis of an anti-hypertensive effect. However, the fact glitazone reduces blood pressure in the human with no diabetes and an animal model of hypertension having no connection with insulin resistance indicates that the anti-hypertensive effect of PPAR gamma agonists is independent of insulin-sensitizing actions.

Since PPAR gamma is expressed in intra-vascular endothelial cells, the PPAR gamma agonists are considered as improving hypertension by regulating the expression of vascular factors connected with the maintenance of vascular tone, such as type C nutriuretic peptide, endothelin, and plasminogen activator inhibitor-1 (Itoh H. et al., 1999).

Furthermore, the proliferation inhibition and pro-differentiation effects of the PPAR gamma agonists suggest that these compounds can be used as an agent for inhibiting the proliferation of de-differentiated tumor cells. This hypothesis supports the experimental results showing that transplantation of BNX triple immuno-deficient nude mice with breast cancer cells (Elstner E. et al., 1998) and prostate tumor cells (Kubota T. et al., 1998) followed by treatment with TZDs inhibits the proliferation of such tumor cells.

These effects show that a differentiation program according to the result of PPAR-mediated activation can be used even in nonadipogenic lineage colonic cells and inhibits the development of cancer. In contrast, when a transformed experimental mouse deficient in one copy of a gene coding for an APC (adenomatous polyposis coli tumor suppressor is treated with PPAR gamma agonists of a significantly higher amount than one required to increase insulin activity, the PPAR gamma agonists promote the development of colonic tumor (Lefebvre A. M. et al. 1998). A human colon cancer cell line studied by Sarraf and his research team has both normal and malfunctioning APCs, and it is considered that many unknown factors required for colonic cell proliferation in an experimental rat model are involved therein.

Furthermore, a recent study conducted by Pilot showed that administering the PPAR gamma agonists to patients with solid liposarcoma caused antineoplastic pro-differentiation. These agonists reduce the proliferation rate of cancer cells, and thus, it is expected that they will make the progression of this disease slow. In any human colon cancers, it was observed that functions of PPAR gamma were lost due to the PPAR gamma mutation (Sarrf P. et al., 1999). The PPAR gamma agonists induce growth arrest and also the synthesis of different markers of human colon cancer cells in cell culture. This discovery suggests that PPAR gamma inhibits cellular transformation.

Moreover, it is found that the PPAR agonists can be used as inhibitors against angiogenesis, a process necessary for solid-tumor growth, and a metastasis process. Thus, such evidences show that PPAR gamma activation inhibits the growth and development of cancer, and PPAR gamma ligands or agonists will provide a new aim for therapeutic application.

Meanwhile, immunoassays are used for detecting such substances.

Generally, immunoassays using antigen-antibody reaction are known as methods of qualitatively and quantitatively analyzing a biological substance to be measured, in which a specific antibody to an antigen substance to be measured is made such that it can be bound to the antigen, and the binding of the antibody to the antigen is measured with various labels which can recognize and measure the antigen-antibody complex with a device.

Immunoassays of biological substances which have been used till now can be divided according to the kind of used labels into radioimmunoassay (RIA) using radioactive isotopes as labels, and non-radioactive immunoassays, including enzyme-linked immunosorbent assay (ELISA) using enzymes or fluorescent substances as labels, and fluorescence enzyme immunoassay (FEIA).

The radioimmunoassay among such immunoassays is widely used which shows high sensitivity and is carried out in a precise, simple, easy and rapid manner. Also it has another advantage in that instruments, such as gamma and beta counters, which can be used in this method, are not so expensive.

However, the greatest shortcoming of the immunoassay using radioactive isotopes is that radioactive wastes are released at large amounts. Also this immunoassay is disadvantageous in that the amount of use and the kind of radioactive isotopes are limited by regulations.

In order to solve such problems, enzyme-linked immunosorbent assay (ELISA) is used which is divided into direct ELISA and indirect ELISA according to a labeling type.

Direct ELISA is a way of conducting direct labeling to an antibody or an antibody fragment by a crosslinker, and indirect ELISA is a way of binding hapten to an antibody and conducting measurement using a label recognizing this complex.

Examples of the crosslinker which is used in the direct ELISA includes N,N'-orthophenylenedimaleimide, 4-(N-maleimidomethyl)cyclohexane-N-succinimide ester, 6-maleimidohexane-N-succinimide ester, 4,4-dithiopyridine and the like. Examples of hapten which is used in the indirect ELISA include biotin, dinitrophenyl pyridoxal, fluoresamine and the like, in which biotin uses avidin or streptoavidin as a recognition ligand.

Horseradish peroxidase is mainly used as an enzyme in ELISA, because it can react with many substrates and can be easily bound to an antibody.

In order to verify a labeled enzyme, horseradish peroxidase uses hydrogen peroxide ($H_2O_2$) as a substrate solution, and 2,2'-azino-di-[3-ethylbenzothiazoline sulfonic acid] ammonium salt (ABTS), 5-aminosalicylic acid, orthophenylenediamine, 4-aminoantipyrine, or 3,3',5,5'-tetramethyl-benzidine as a color developer. Also, alkali phosphatase employs orthonitrophenyl phosphate or paranitrophenyl phosphate as a substrate, and β-D-galactosidase uses fluorescein-di-(β-D-galactopyranoside) or 4-methylumbellifery as a substrate.

Meanwhile, if a substance immobilized to a plate is an antibody, ELISA is also called a sandwich ELISA.

DISCLOSURE OF INVENTION

Accordingly, an object of the present invention is to provide a specific monoclonal antibody for PPAR gamma, and a hybrodoma cell line producing the same.

Another object of the present invention is to provide a method for detecting a regulator related to inflammation, cancer and metabolic diseases using a specific monoclonal antibody for PPAR gamma, and a kit for use in the method.

To achieve the above-mentioned objects, in one aspect, the present invention provides a Pγ48.34A cell line (KCTC 10482BP), which produces a monoclonal antibody whose immunoglublulin subtype is $G_{2a}$, the monoclonal antibody having having specific immunoreactivity for human and mouse PPAR gamma proteins.

In another aspect, the present invention provides a monoclonal antibody produced by this cell line.

In still another aspect, the present invention provides a method for detecting a regulator related to cancer, inflammation and metabolic diseases, the method comprising the Steps of: coating a PPAR gamma coactivator on a plate; adding a sample containing a PPAR gamma protein and a candidates related to cancer, inflammation and metabolic diseases to the plate; adding a monoclonal antibody to the plate so that the antibody binds to the PPAR gamma protein; adding an antibody having immunoreactivity for the monoclonal antibody and labeled with an enzyme to the plate; and detecting the label and measuring the concentration of the PPAR gamma protein, thereby determining if the regulator related to cancer, inflammation and metabolic diseases is present in the sample.

In yet another aspect, the present invention provides a kit for detecting a ligand related to cancer, inflammation and metabolic diseases by immunoassay, the kit comprising: a coactivator protein coated on a plate; a PPAR gamma protein capable of binding to the coactivator protein; a monoclonal antibody having specific immunoreactivity for the PPAR gamma protein; and an antibody labeled with an enzyme and having immunoreactivity for the monoclonal antibody.

Preferably, the PPAR gamma protein is PPAR gammal or PPAR gamma2, and the coactivator is SRC-1 (steroid receptor coactivator).

Hereinafter, the present invention will be described in detail.

The present invention provides a specific monoclonal antibody for PPAR gamma related to inflammation, cancer and metabolic diseases (obesity and diabetes), and a hybridoma cell line producing the monoclonal antibody. Also the present invention provides a method for detecting a regulator capable of regulating the PPAR gamma activity, by means of the specific monoclonal antibody for the PPAR protein, and a kit using this method.

According to the present invention, in order to produce the specific monoclonal antibody for PPAR gamma and the hybridoma cell line producing the same, PPAR gamma2 cDNA was isolated from human lipoma, amplified and purified. After cloning into an E. coli expression vector, it is expressed into a fusion protein (hereinafter, referred to as His-PPAR gamma2 and GST-PPAR gamma2) in E. coli, and isolated and purified on nickel beads, thereby producing an antigen for the antibody.

And, a His-PPAR gamma2 soluble protein is emulsified with an equal amount of a Freund's complete adjuvant and inoculated into the abdominal cavity of a mouse required for the development of a hybridoma cell line. After two weeks, to increase immunity, the mouse receives a booster injection, in which a His-PPAR gamma2 soluble protein is mixed with an equal amount of a Freund's incomplete adjuvant and injected into the abdominal cavity of the mouse in two times.

A spleen cell taken from the immunized mouse and a NS-1 myeloma cell are mixed with each other at the ratio of 10:1, and fused by the addition of polyethylene glycol. The cells are cultured in HAT medium, and when the growth of the fusion cells is continuously confirmed, the cells are proliferated in HT medium. Among the cells growing in the HAT medium, cells which specifically react only with the PPAR gamma recombinant protein are screened by enzyme-linked immunosorbent assay (ELISA).

The screened hybridoma cell line is cloned as a monoclone by a limiting dilution technique, thereby establishing a cell line consisting of cells proliferated from one cell.

The established cell line of the present invention was termed Pγ48.34A, and deposited under the accession number KCTC 10482BP on Jun. 3, 2003 with the Korean Collection for Type Cultures (KCTC).

After the cell line is injected into the abdominal cavity of the mouse, ascitic fluid is taken from the mouse, thereby producing the monoclonal antibody of the present invention at large amounts.

The isotype of the PPAR gamma protein-specific monoclonal antibody, which is secreted by the cell line established in the present invention, is an immunoglobulin $G_{2a}$ ($IgG_{2a}$) isotype. As confirmed by Western blotting and immunoprecipitation, the cell line developed by the present inventors shows high specificity for human and mouse PPAR gamma proteins. Also, as confirmed by Western blotting of other commercially available specific monoclonal or multiclonal antibodies for PPAR gamma, the cell line of the present invention has no cross-reactivity with other isotypes of PPAR, such as PPAR alpha, delta and beta.

According to the present invention, an enzyme-linked immunosorbent assay (ELISA) method was constructed. In this ELISA, the conformation of PPAR gamma in the binding of PPAR gamma and SRC-1 protein known as an agonist for PPAR gamma is induced, and using properties of agonist or antagonist ligands influencing the binding between PPAR gamma and SRC-1, a regulator related to inflammation, cancer and metabolic diseases is detected from a mixture containing the monoclonal antibody, the PPAR gamma recombinant protein, the SRC-1 recombinant protein and various candidates such as natural and artifactual compound.

According to the present invention, the SRC-1 recombinant protein is isolated from E. coli, purified, and attached to a microtiter plate and then reacted with a human PPAR gamma2 fraction expressed into GST- and His-fusion proteins in E. coli., so that a change in binding activity caused by transformation of the PPAR gamma protein with natural substances and various chemicals is examined. As a result, it was found that the use of the specific monoclonal antibody for PPAR gamma, developed by the present inventors, allowed a PPAR gamma regulator to be detected in a more precise and reliable manner than other commercially available specific antibodies for PPAR gamma.

BEST MODE FOR CARRYING OUT THE INVENTION

The present invention will hereinafter be described in further detail by examples. It should however be borne in mind that the present invention is not limited to or by the examples.

Example 1

Preparation of Expression Vector Producing PPRA gamma Recombinant Protein, and Isolation and Purification of Recombinant Protein To obtain a PPAR gamma recombinant protein, a human PPAR gamma2 cDNA gene was used. This gene was obtained by isolating mRNA from human lipoma and then amplifying it by reverse transcription-PCR. An expression vector pET28a (Novagen) was cleaved with BamH I and Xho I restriction enzymes, and the gene was ligated into the vector by lagase at 16° C. for 5 hours, thereby producing an expression vector having the PPAR gamma2 gene.

Figure 1:
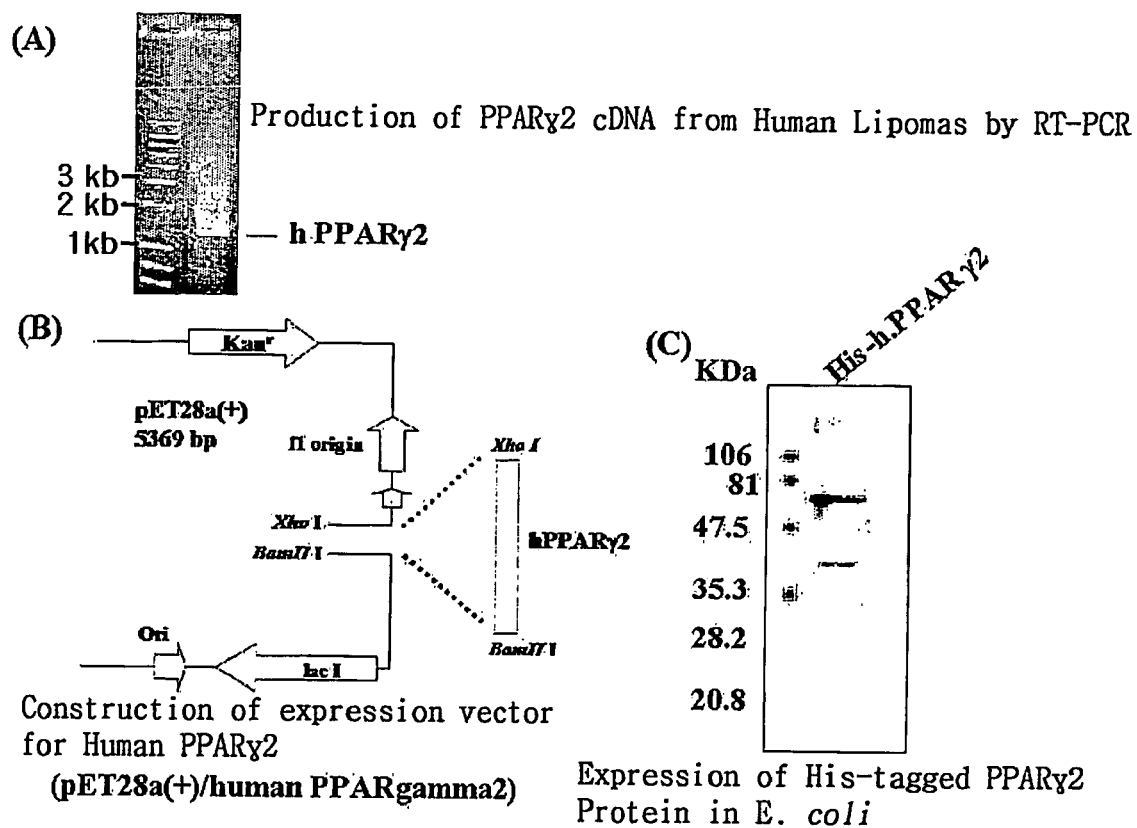
FIG. 1A shows the analysis of amplified cDNA of PPAR gamma2 on 1% agarose gel. The cDNA was obtained by isolating mRNA from human lipoma, reverse-transcripting mRNA to cDNA using reverse transcriptase and amplifying cDNA with PPAR gamma2 primers.
FIG. 1B is a schematic view showing that PPAR gamma2 is cloned into an E. coli expression vector to mass-produce the PPAR gamma2 protein in E. coli.
FIG. 1C shows the results of analysis of His-fused PPAR gamma2 on 12% SDS-PAGE. The His-fused PPAR gamma2 was amplified, isolation and purified in E. coli.

The expression vector pET28a, which can express a 6-histine-tagged PPAR gamma protein, was transformed in *E. coli* BL21(DE3), and then shake-cultured at 37° C. in LB medium containing 100 μg/ml kanamycin antibiotic. When the absorbance at 600 nm reached 0.4-0.6, the culture solution was added with 1 mM IPTG (isopropylthio-β-D-galactoside), and cultured overnight at 20° C., thereby inducing the expression of the gene. The resulting culture solution was centrifuged at 4° C. and 6,000 rpm for 20 minutes, and the transformed *E. coli* was collected. The collected *E. coli* was completely disrupted in cell lysis buffer (20 mM Tris, pH 7.4, 300 mM NaCl, 10 mM imidazol, 5 μg/ml aprotinin, 100 μM PMSF) with an ultrasonic homogenizer. The disrupted solution was centrifuged at 4° C. and 12,000 rpm for 30 minutes, and the supernatant was collected. The collected supernatant was loaded onto NTA agarose (Peptrone) beads having an affinity for the histidine residues so that His-PPAR gamma2 was bound to the beads. To reduce non-specific binding, the beads were washed three times with washing solution (20 mM Tris, pH 7.4, 300 mM NaCl, 20 mM imidazol). The recombinant protein bound to the beads was separated with eluant (20 mM Tris, pH 7.4, 300 mM NaCl, 200 M imidazol). The eluted solution was separated by electrophoresis on 12% SDS-PAGE gel to examine the eluted protein. The results are shown in FIG. 1. As shown in FIG. 1, it could be found that the protein was His-PPAR gamma2 recombinant protein with a 55 kDa molecular weight.

Example 2

Isolation and Purification of GST-fused PPAR gamma2 and His-SRC-1 Recombinant Proteins To produce a GST-PPAR gamma2 recombinant protein, there was used *E. coli* (pGEX4T-1/PPARγ 2; KCTC 10190BP) which had been transformed with expression vector pGEX4T-1 (Pharmacia) cloned with the PPAR gamma2 gene of Example 1.

Under conditions of over-expression and efficient production of a recombinant protein, *E. coli* was cultured. The cultured *E. coli* was disrupted with ultrasonic waves, and centrifuged and the supernatant was collected. A soluble fraction of the supernatant was directly used.

Meanwhile, a SRC-1 protein was obtained as follows.

*E. coli* (pET28a/SRC-1; deposited on Feb. 22, 2002, in the Korean Type Tissue Collection (KCTC), located at Korea Research Institute of Bioscience and Biotechnology, #52, Oun-dong, Ysusong-ku, Taejon 305-333, Republic of Korea under accession number KCTC 10191BP) producing a His-tagged SRC-1 protein was cultured, disrupted with ultrasonic waves, and then centrifuged, and the supernatant was collected and loaded onto NTA agarose (Peptron Inc., Daejeon, Korea) beads so that His-PPAR gamma2 was bound to the beads. To reduce non-specific binding, the beads were washed three times with cell lysis buffer (20 mM Tris, pH 7.4, 300 mM NaCl, 20 mM Imidazol). The recombinant protein bound to the beads was separated with eluant (20 mM Tris, pH 7.4, 300 mM NaCl, 200 mM Imidazol) and purified. The expression condition and method as described above were the same as Example 1, and thus, a method for examining the binding between PPAR gamma2 and SRC-1 was established and could be used as an efficient screening system for the design and development of new substances which can influence the binding between PPAR gamma2 and SRC-1.

Example 3

Mouse Immunization

To obtain an immunized mouse required for the production of a hybridoma cell line, His-PPAR gamma2 produced in Example 1 was dialyzed against phosphate solution for 12 hours, and the protein concentration was quantified to 25 μg/100 μl by the Bradford method. Then, it was emulsified with an equal volume of a Freund's complete adjuvant and injected into the abdominal cavity of a Balb/c mouse (six weeks old). After two weeks, a His-PPAR gamma2 recombinant protein of the same amount as the first inoculation, which had been mixed with the same amount of a Freund's incomplete adjuvant, was injected to the mouse once a week. At 3 or 4 days after the last injection, a small amount of blood was collected from the mouse tail, and measured for antibody titer by enzyme-linked immunosorbent assay (ELISA). Before cell fusion, the mouse additionally received one injection.

Example 4

Cell Fusion

The mouse immunized according to Example 3 was fractured at its cervical vertebral. And the spleen was drawn from which fat tissues were removed and finely ground with a homogenizer. The resulting material was centrifuged in RPMI-1640 medium, and spleen cells were collected. At this time, to make the spleen cells pure, leukocyte lysis buffer was used and the spleen cells were sufficiently washed two times with RPMI-1640 medium.

Meanwhile, at two weeks before cell fusion, NS-1 myeloma cells, parent cells for cell fusion, were cultured in RPMI-1640 medium containing 10% fetal bovine serum (FBS). The NS-1 cells were washed twice in RPMI-160 medium. The spleen cells and the parent cells were counted and mixed at the ratio of 7:10. After mixing, the cells were precipitated by centrifugation. The precipitate in a centrifuge tube was dispersed by patting it with a finger, and lightly shaken, adding 1 ml polyethylene glycol over one minute. Then it was filled with 50 ml of RPMI-1640 medium, centrifuged and washed two times. The resulting precipitate was re-suspended in 20-40 ml of isolation medium (HAT medium) containing 10% fetal bovine serum. 200 μl of the suspension was added to each well of a 96-well plate, and then cultured in a $CO_2$ incubator at 37° C.

Example 5

Screening of Hybridoma Cell Line Producing Monoclonal Antibody

The cells fused in Example 4 were cultured for about two weeks, and then, among the produced fusion cells, fusion cells secreting a specific antibody for PPAR gamma were screened.

Figure 2:
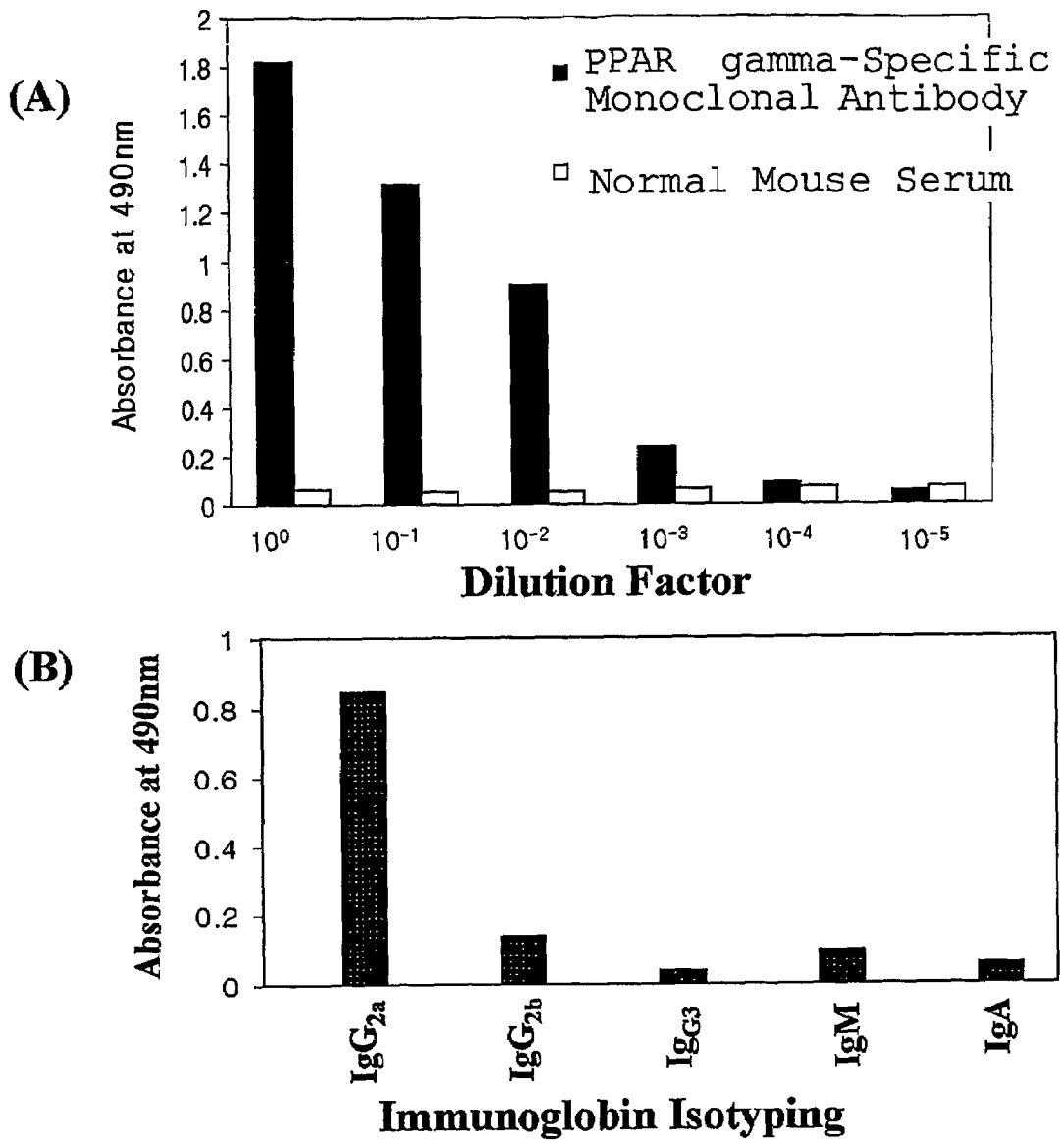
FIG. 2A shows that a monoclonal antibody has a high affinity for GST-fused PPAR gamma2 as an antigen.
FIG. 2B shows the isotype of a PPAR gamma-specific monoclonal antibody, which was examined by an isotyping kit (Immuno-Type™ mouse monoclonal antibody isotyping kit, BD science).

A GST-fused PPAR gamma2 recombinant protein was isolated and purified. The purified protein was used as an antigen in enzyme-linked immunosorbent assay (ELISA). The use of the GST-fused PPAR gamma2 recombinant protein is to eliminate fusion cells secreting a histidine-specific antibody, since a His-tagged PPAR gamma2 recombinant protein was used as an antigen upon immunization of the mouse. The GST-fused PPAR gamma2 recombinant protein was prepared in a similar manner to the His-tagged protein, using expression vector pGEX4T-1 (Amersham Pharmacia) as described in Example 2. 50 µl (8 g/ml) of the GST fused PPAR gamma2 recombinant protein was loaded onto each well of a mircotiter plate, and unreacted antigens were blocked with skimmed milk. Then, 50 (1 of the culture solution of fusion cells was added to each well of the plate and allowed to react at room temperature for one hour. Then it was washed three times with phosphate buffer saline (containing 0.05% Tween®-20), and goat anti-mouse IgG-horseradish peroxidase (HRP; Sigma) was added. The mixture was allowed to react at room temperature for one hour and washed, and peroxidase substrate (OPD) was added. The color reaction was measured at the absorbance at 490 nm. On the basis of the experimental results, fusion cells secreting an antibody having high binding force to the PPAR gamma2 recombinant protein were screened, and the screened cells were subjected to the above processes several times. Thus, among various fusion cells, a fusion cell population, which has the highest binding force and specifically reacts, was re-screened. The screened fusion cell was diluted to a monoclone by limiting dilution, thereby discovering a hybridoma cell line producing a monoclonal antibody originated from one cell. This hybridoma was deposited under the accession number KCTC 10482BP with the Korean Collection for Type Cultures (KCTC). The hybridoma cell line (KCTC 10482BP) producing a monoclonal antibody was cultured, and antibody titer was determined by enzyme-linked immunosorbent assay (ELISA). The results are shown in FIG. 2A.

Furthermore, the immunoglobulin isotype of the monoclonal antibody produced in the hybridoma cell line was determined using an Immuno-™ Mouse Monoclonal Antibody Isotyping Kit (BD Bioscience). As shown in FIG. 2B, it could be found that the immunoglobulin isotype of the specific monoclonal antibody for PPAR gamma was G2a.

Example 6

Mass Production of Monoclonal Antibody

Example 6 is given to illustrate the mass production of a specific monoclonal antibody for PPAR gamma from the hybridoma cell line established in Example 5.

100 (1 of a Freund's incomplete adjuvant was injected into the abdominal cavity of an experimental mouse (Balb/c). After one week, 5×105 fusion cells were injected into the mouse, and ascitic fluid was collected when the abdominal cavity was swollen up. Since the ascitic fluid contained grown fusion cells at high concentration, it was centrifuged at 10,000 rpm to precipitate the fusion cells, and only the supernatant was collected. The supernatant was separated by Protein A agarose affinity column (Bio Rad), dialyzed against phosphate buffer and stored at −70 (C.

Example 7

Confirmation of Antigen-antibody Reaction of Inventive Monoclonal Antibody in Recombinant Protein, Cell Line and Tissue In this example, using a specific monoclonal antibody for PPAR gamma obtained in Example 6, a 55 kDa PPAR gamma recombinant protein present in a recombinant protein, a cell line and a tissue was subjected to Western blotting. In this case, E. coli lysate was used from which human and mouse His-tagged PPAR gamma2 recombinant proteins had not been not isolated and purified.

Figure 3:
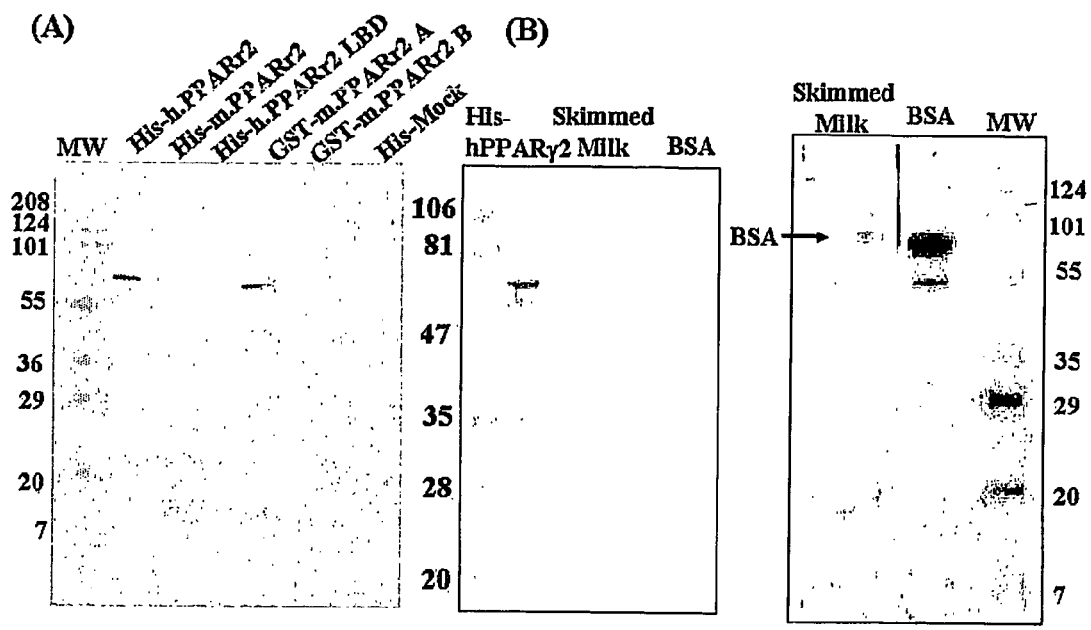
FIG. 3A shows the result of Western blotting analysis of human and mouse His-fused recombinant proteins.
FIG. 3B shows the results of Western blotting analysis indicating that a Pγ48.34A antibody developed by the present inventors shows non-specific reaction with skimmed milk and BSA whereas some of existing PPAR gamma-specific antibodies react with skimmed milk and BSA.

The E. coli lysate was centrifuged. The supernatant was suitably diluted and separated by 12% SDS-PAGE, and the separated protein was transferred to a membrane filter. To reduce non-specific reaction that other proteins show in the membrane filter, the membrane was blocked with 5% skimmed milk for 2 hours. Then the specific—monoclonal antibody for PPAR gamma developed by the present inventors was added to the membrane filter and allowed to react for one hour. Then it was washed with phosphate buffer saline (containing 0.05% Tween®-20), and goat anti-mouse IgG-alkaline phosphatase (AP) (Sigma) was added and allowed to react at room temperature for one hour. Then, the membrane filter was sufficiently washed and the color was developed with alkaline phosphatase substrate (Promega). FIG. 3A shows that the monoclonal antibody specifically reacts with human PPAR gamma without binding to His, and FIG. 3B shows that the monoclonal antibody of the present invention does not react with skimmed milk and also bovine serum albumin (BSA). Some of other commercially available PPAR gamma antibodies react with BSA. As a result, it could be found that the monoclonal antibody of the present invention does not have non-specific reaction and was very specific for PPAR gamma.

Meanwhile, it could be found that PPAR gamma was expressed in a mouse 3T3-L1 cell line, a fat cell line. To confirm this expression, Western blotting was used. As the 3T3-L1 cell line, cells which had been differentiated with 1 µg/ml insulin and 30 uM indomethacine and had not been differentiated were used. The use of these cells is to confirm that PPAR gamma is expressed in the differentiated cell line at a larger amount. An eluate containing the cytoplasm and nucleus of the cells was obtained, and an equal amount of the protein was separated by 12% SDS-PAGE, and subjected to Western blotting.

Figure 4:
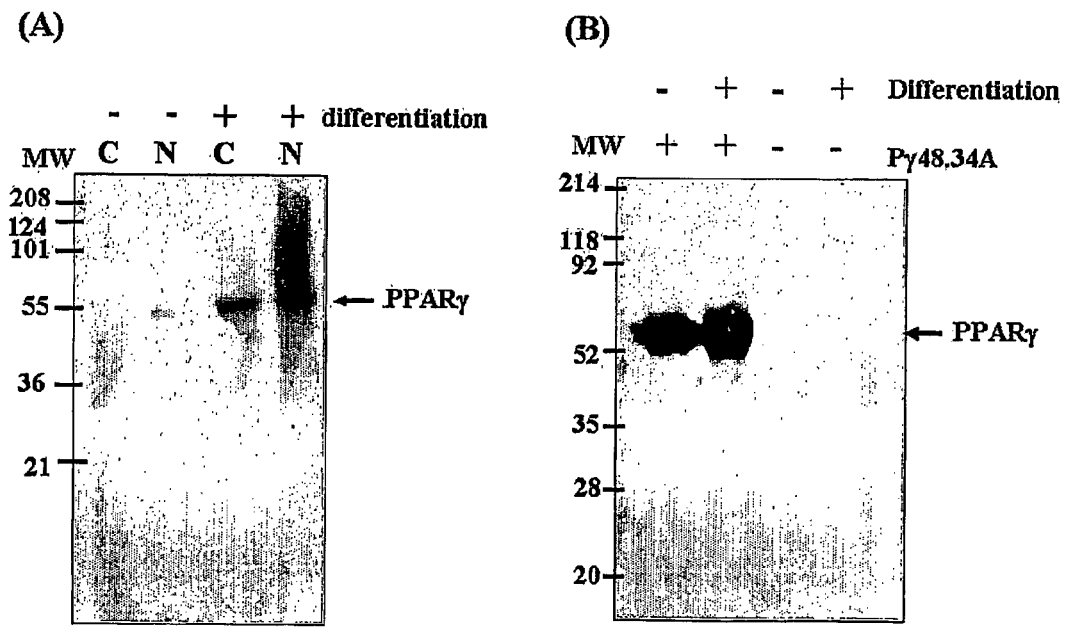
FIG. 4A shows the results of the Western blotting analysis of PPAR gamma using a mouse 3T3-L1 cell line.
FIG. 4B shows that a PPAR gamma-specific antibody (Pγ48.34A) can also be used in immunoprecipitation of a 55 kDa PPAR gamma regardless of fat differentiation.

Color development was performed by ECL regent (Pharmacia-Amersham). FIG. 4A shows that PPAR gamma is expressed in the differentiated mouse.

FIG. 4B shows that antigen-antibody reaction of the specific monoclonal antibody for PPAR gamma occurs in the mouse 3T3-L1 cell line by immunoprecipitation.

The experiment in FIG. 4B was carried out as follows.

5 µl of the specific monoclonal antibody for PPAR gamma was added to the eluate containing the cytoplasm and intranuclear protein of the differentiated and non-differentiated cells, and allowed to react at 4° C. for one hour. And, the mixture was added to 10 µl protein-A agarose beads and allowed to further react at 4° C. for 30 minutes. An antigen-antibody complex bound to the beads was washed three times and purified by centrifugation. Then, the complex was added to 5-fold sample-loaded buffer and warmed in boiling water for 5 minutes. And, it was separated by 12% SDS-PAGE, transferred to a membrane filter and subjected to Western blotting with the specific monoclonal antibody for PPAR gamma.

As described above, it can be found that the PPAR gamma-specific monoclonal antibody produced by the present inventors can be used in Western blotting and also immunoprecipitation.

To compare the specificity and binding of the PPAR gamma specific monoclonal antibody (Pγ48.34A) of the present invention to those of commercially available PPAR gamma-specific antibodies, the following test was conducted.

Figure 5:
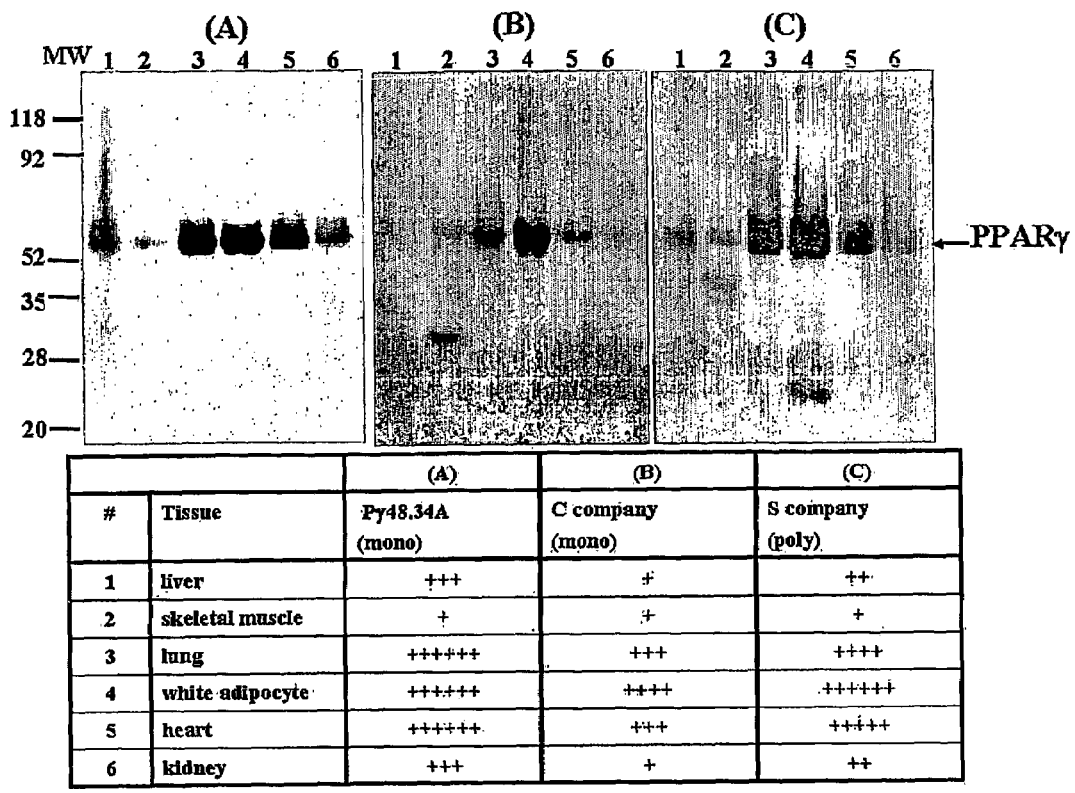
FIG. 5A shows the non-specific binding of a Pγ48.34A monoclonal antibody constructed by the present inventors.
FIG. 5B shows the non-specific binding of a PPAR gamma-specific multiclonal antibody (cat. 516555 produced by Calbiochem.).
FIG. 5C shows the non-specific binding of a PPAR gamma-specific antibody (sc-7273 produced by Santacruz).

First, various tissues of a mouse were collected and lysated in cell lysis buffer (20 mM Hepes, 300 mM NaCl, 1 mM EDTA, 1 mM PMSF, 0.1% NP40, pH 7.5). The lysated cells were centrifuged at 12,000 rpm, and the supernatant was collected. The protein concentration of the cell lysate was determined by Bradford protein assay, and each 100 μg of the cell lysate was loaded for 12% SDS-PAGE. After electrophoresis, it was subjected to Western blotting with the PPAR gamma-specific Pγ48.34A antibody of the present invention, a specific multiclonal antibody for PPAR gamma (cat. 516555 made by Calbiochem company), and a specific monoclonal antibody for PPAR gamma (sc-7273 made by Santacruz company). The test results are shown in FIG. 5. From FIG. 5, it could be found that the Pγ48.34A monoclonal antibody of the present invention showed significantly reduced non-specific binding and more excellent binding as compared to other company's products.

Example 8

Mechanism of PPAR gamma2 and SRC-1 Proteins in Cells and Principle of ELISA Using It PPAR gamma2 is specifically expressed in fat cells, binds to RXR alpha to form heterodimers, and binds to PPRE (PPAR response elements. This complex is a transcriptional regulator which binds to transcriptional factors in a complex manner to promote the transcription of a target gene. Its transcriptional activity is determined depending on whether it has hydrophobic low molecules (agonists) or not.

When 15d-PGJ2 or TZDs, currently known PPAR gamma ligands, binds to PPAR gamma, their binding force to SRC-1 protein, a coactivator, is reduced due to the transformation of PPAR gamma protein itself. These ligands increase the half-life of PPAR gamma in cells, and further increase the transcription of a target gene by binding to coactivators. The ligands capable of increasing the binding force between PPAR gamma and SRC-1 are called agonists whose possibility for use as anti-cancer agents and anti-inflammatory agents is being increased.

Particularly, TZDs are marketed as agents for treating type 2 diabetes.

Figure 6:
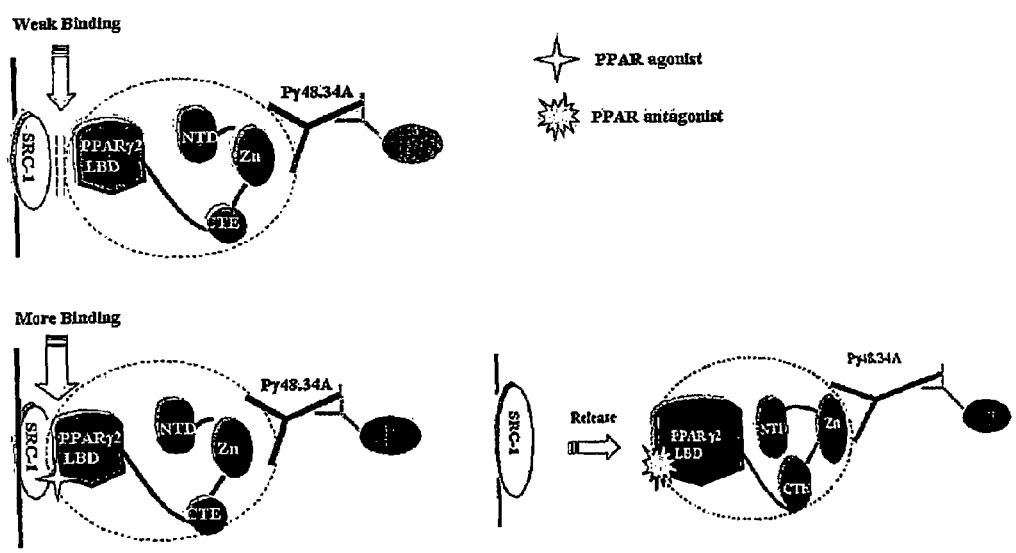
FIG. 6 schematically shows the principle of ELISA (enzyme-linked immunosorbent assay) for detecting PPAR regulators related to inflammation, cancer and metabolic diseases, using a monoclonal antibody of the present invention, GST-fused PPAR gamma protein and His-fused SRC-1 (steroid receptor coactivator).

By applying such intracellular mechanisms in ELISA, the present inventors have developed a method for detecting PPAR gamma agonists or PPAR gamma ligands, which is more easily conducted and allows many samples to be received. As shown in FIG. 6, this method comprises coating SRC-1 proteins on an ELISA plate, treating E. coli lysate containing GST-PPAR gamma with a sample, and determining the binding between SRC-1 and PPAR gamma using Pγ 48.34A, a specific monoclonal antibody for PPAR gamma.

If substances which can be PPAR gamma agonists are present in the treated samples, the binding shown by an ELISA reader will be a higher numerical value than a control group. On the other hand, if there are antagonists inhibiting the binding therebetween, he binding shown by the ELISA reader will be a lower numerical value than the control group.

Example 9

Figure 7:
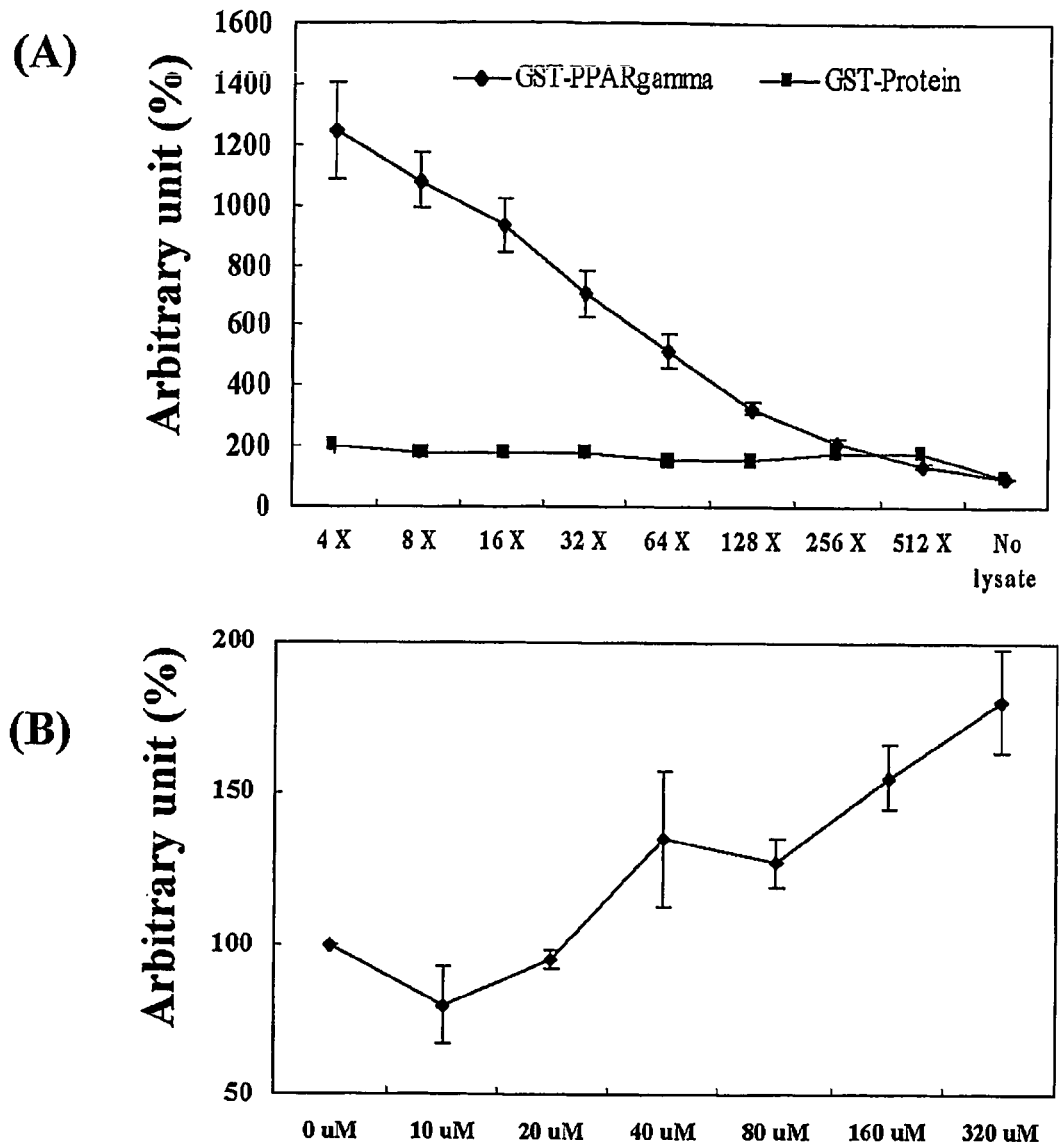
FIG. 7A shows that the binding between SRC-1 and PPAR gamma2 is dependent on PPAR gamma concentration.
FIG. 7B shows that the binding between PPAR and SRC-1 is increased by the addition of indomethacin. From the fact the binding between the two proteins is increased in a ligand concentration-dependent manner at the same protein concentration, it can be found that ELISA using a PPAR gamma-specific antibody can be a good way for detecting regulators related to diseases, such as inflammation, cancer and metabolic diseases.

Effect of PPAR gamma2 and Ligand Concentrations on Binding between SRC-1 and PPAR gamma2 Proteins in ELISA To examine the effect of PPAR gamma2 protein concentration on the binding between SRC-1 and PPAR gamma2 proteins, the following test was conducted. As shown in FIG. 7A, 0.8 μg/ml SRC-1 was coated on a plate, and E. coli lysate containing GST-PPAR gamma2 was diluted 512-, 256-, 128-, 64-, 32-, 16-, 8- and 4-fold and added to the plate. Also, this procedure was repeated three times, and a GST-fused protein which had not been bound to SRC-1 protein was used as a control group. As shown in FIG. 7A, it could be found that the binding between SRC-1 and PPAR gamma2 proteins in ELISA was dependent on the concentration of PPAR gamma2. Furthermore, to examine the effect of PPAR gamma2 ligand concentration on the binding between SRC-1 and PPAR gamma2 proteins, the following test was conducted. 8 μg/ml SRC-1 was coated on a plate, and E. coli lysate was diluted 64-fold and added to the plate. Then, indomethacin, a PPAR gamma2 ligand, was added to the plate at a different concentration.

The results are given in FIG. 7B. As shown in FIG. 7B, it could be found that the binding was dependent on the concentration of indomethacin, a PPAR gamma2 ligand. The results of FIG. 7B were given as an average of the results of more three tests.

Example 10

Establishment of System Capable of Detecting PPAR Ligands using in vitro Binding between Soluble Fractions of GST-PPAR gamma2 and His-SRC-1 Proteins The binding between SRC-1 protein and PPAR gamma in a soluble fraction was measured by ELISA.

His-SRC-1 protein isolated from E. coli and eluted from nickel beads, and purified PPAR gamma-fused protein produced in E. coli, were used as antigens.

His-SRC-1 protein was diluted with 0.1 M sodium carbonate buffer (pH 9.6) to a concentration of about 800 ng/well. 100 μl of the protein dilution was loaded into each well of an ELISA plate, and coated on the plate overnight at 4° C. The coated plate was washed three times with PBS (containing 0.05% Tween®-20), and added with 3% skimmed-PBST solution and left to stand overnight at 4° C. or for 2 hours at room temperature. A soluble fraction of GST-fused PPAR gamma2 was diluted 32-fold, and 50 μl of the dilution was added to each well of the plate. Indomethacin, a PPAR gamma2 agonist, was added at 1 μM, 10 μM and 100 μM.

Figure 8:
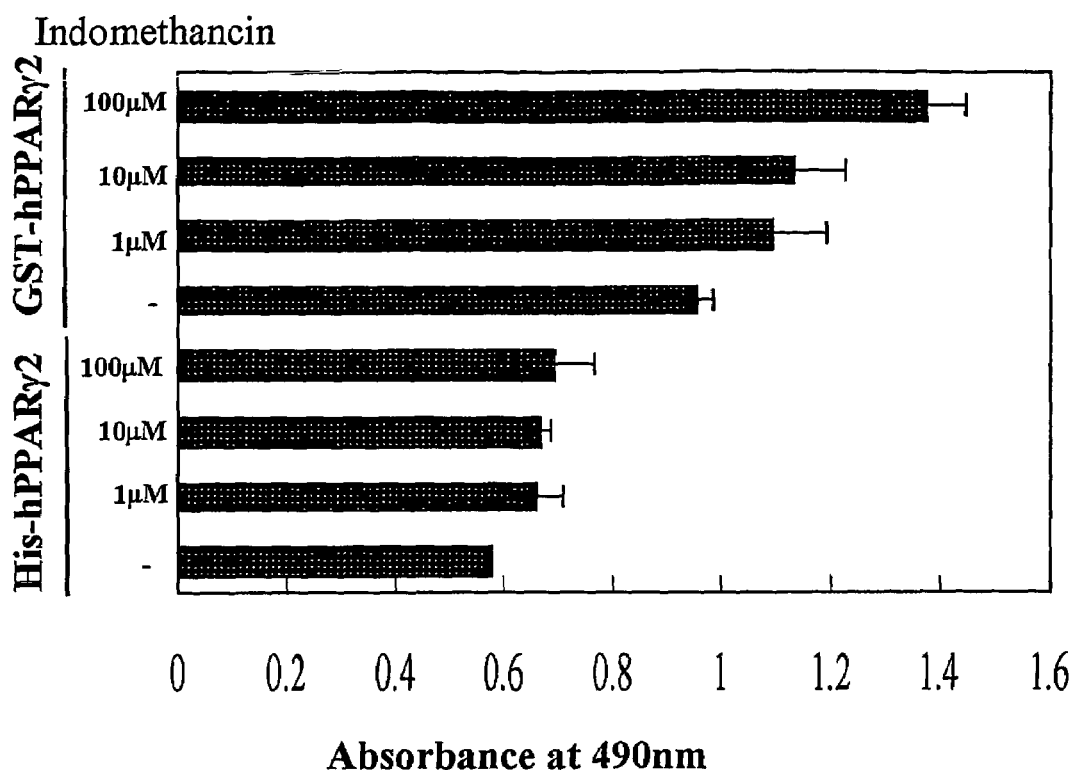
FIG. 8 shows that the specific binding between SRC-1 and PPAR gamma2 is increased by PPAR gamma2-specific transformation. From FIG. 8, it can be found that the use of ligands at concentrations of 1 μM, 10 μM and 100 μM is most suitable, the use of His-PPAR provides better results than using GST-PPAR gamma, and the binding between PPAR gamma and SRC-1 is increased depending on the concentration of ligands.

The plate was subjected to binding reaction at room temperature for one hour with slow stirring, and washed five times with PBS (containing 0.05% Tween®-20). To determine the binding between the His-SRC-1 protein and the GST-fused PPAR gamma2 protein, a monoclonal antibody (P48.34A) which had been developed by the present inventors was 2,000-fold diluted with PBST and used as a primary antibody. An anti-mouse IgG-HRP antibody which had been 2,000-fold diluted was used as a secondary antibody. As a control group, DMSO (dimethylpolysiloxane) in which PPAR gamma2 agonists had been dissolved was added as a negative control for PPAR gamma2 ligands. The control group showed no significant change in the absorbance at 490 nm. The test results are shown in FIG. 8. From FIG. 8, it could be found that the specific binding between SRC-1 protein and the PPAR gamma2 protein was promoted by ligand-specific conformation. Using this principle, an ELISA system capable of screening PPAR gamma2-specific ligands was established.

Example 11

Utility of ELISA Detection Method

The detection method according to the present invention differs from the prior detection method. The present invention provides a screening system which does not use radioactive isotopes, allows an increased number of samples to be used at the same time, and shows results in a more rapid manner. In the present invention, an antibody is used instead of radioactive isotopes, a 96-well plate is used to allow many kinds of samples to be used at the same time, and color development using an enzyme is used so that results can be shown in a more rapid manner than the prior method.

By virtue of such convenience and rapidness, the detection method of the prevent invention will be highly effective in detecting ligands in various functional foods and plant extracts. The detection method of the present invention is a method for detecting PPAR gamma ligands closely related to cancer inhibition, inflammation inhibition, obesity, diabetes, lipid metabolism and cancer. Thus, according to this method, many substances which show effects against such diseases can be primarily detected in a rapid and easy manner.

INDUSTRIAL APPLICABILITY

As described above, the present invention provides a method for primarily detecting regulators related to cancer, inflammation, obesity and diabetes, which is based on the binding between transcriptional factor SRC-1 and PPAR gamma, a nuclear receptor known as having an effect on anti-inflammation and anti-cancer. This method is easily conducted, allows many samples to be applied at the same time, and does not utilize radioactive isotopes. Thus, this method will be advantageously applied for the development of agents for the improvement and treatment of cancer, inflammation, obesity and metabolic diseases.

What is claimed is:

1. A Pγ48.34A cell line deposited under the accession number KCTC 10482BP, which produces a monoclonal antibody whose immunoglobulin isotype is $G_{2a}$, the monoclonal antibody having specific immunoreactivity for human and mouse PPAR gamma proteins.

2. The Pγ48.34A cell line of claim 1, wherein the PPAR gamma proteins are PPAR gamma1 or PPAR gamma2.

3. A monoclonal antibody produced by the cell line of claim 1.

* * * * *

UNITED STATES PATENT AND TRADEMARK OFFICE
CERTIFICATE OF CORRECTION

PATENT NO. : 7,387,895 B2 Page 1 of 1
APPLICATION NO. : 10/543452
DATED : June 17, 2008
INVENTOR(S) : Doyoung Yoon It is certified that error appears in the above-identified patent and that said Letters Patent is hereby corrected as shown below:

On the Title page item 54, and Col. 1, line 2, Delete "HYDRIDOMA" and insert --HYBRIDOMA-- therein.

Signed and Sealed this

Twelfth Day of August, 2008

JON W. DUDAS
*Director of the United States Patent and Trademark Office*